United States Patent
Viaud et al.

(10) Patent No.: US 6,620,809 B2
(45) Date of Patent: Sep. 16, 2003

(54) SUBSTITUTED (DIHYDRO)BENZOXAZINE AND (DIHYDRO)BENZOTHIAZINE COMPOUNDS

(75) Inventors: Marie-Claude Viaud, Tours (FR); Gérald Guillaumet, Saint Jean le Blanc (FR); Philippe Daubos, La Loupe (FR); Caroline Bennejean, Charenton le Pont (FR); Philippe Delagrange, Issy les Moulineaux (FR); Pierre Renard, Le Chesnay (FR)

(73) Assignee: Les Laboratoires Servier, Neuilly-sur-Seine (FR)

(*) Notice: Subject to any disclaimer, the term of this patent is extended or adjusted under 35 U.S.C. 154(b) by 5 days.

(21) Appl. No.: 09/730,119

(22) Filed: Dec. 5, 2000

(65) Prior Publication Data

US 2001/0003747 A1 Jun. 14, 2001

(30) Foreign Application Priority Data

Dec. 6, 1999 (FR) .............................. 9915309

(51) Int. Cl.[7] .................. C07D 265/36; C07D 279/16; A61K 31/538; A61K 31/542; A61P 25/24
(52) U.S. Cl. ................ 514/230.5; 544/105; 544/51
(58) Field of Search .................. 544/105; 514/230.5

(56) References Cited

PUBLICATIONS

Doolen, et al., European Journal of Pharmacology, 1998, 345, 67–69.
Pintor, et al., European Journal of Pharmacology, 2001, 416, 251–254.
Lagneux, et al., Life Sciences, 2000 66(6), 503–509.
Geary, et al., Society for Neuroscience, 1996 22, 910.
Régrigny, et al., Fundamental and Clinical Pharmacology, 2001, 15, 233–238.
Kitamura, et al., Journal of Human Hypertension, 2002 16, 193–197.
Hunt, et al., Am. J. Physiol. Cell Physiol., 2001, 280, C110–C118.
American Psychiatric Association: *Diagnostic and Statistical Manual of Mental Disorders*, Fourth Edition. Washington, DC, American Psychiatric Association, 1994.
M. Dahlitz, et al. Delayed Sleep Phase Syndrome Response to Melatonin. The Lancet 1991;337:1121–1124.
Robert L. Sack, et al. Melatonin Administration to Blind People; Phase Advances and Entrainment. Journal of Biological Rhythms 1991;6(3):249–261.
Keith Petrie, et al. A Double–Blind Trial of Melatonin as a Treatment for Jet Lag in International Cabin Crew. Biol. Psychiatry 1993;10(5):315–320.
Simon Folkard, et al. Can Melantonin Improve Shift Workers' Tolerance of the Night Shift? Some Preliminary Findings. Chronobiology International 1993;10(5):315–320.
Giora Pillar, et al. Melatonin Improves Sleep–Wake Patterns in Psychomotor Retarded Children. Pediatric Neurology 2000;23(3):225–228.
Lars Palm, Gösta Flennow, and Lennart Wetterberg. Correction of Non–24–Hour Sleep/Wake Cycle by Melatonin in a Blind Retarded Boy. Annals of Neurology 1991;29(3):336–339.
Goodman and Gilman's: *The Pharmacological Basis of Therapeutics*, Eighth Edition. Pergamon Press, New York, 1990.
National Institute of Health/ National Center on Sleep Disorders Research/ The National Cancer Institute. "Overview of Sleep Disorders", obtained from PDQ, the NCI's comprehensive information database.
The American Academy of Sleep Medicine (AASM). "Assessment and Management of Sleep Disorders in Primary Care Practice", obtained from the AASM information database.
National Institute of Mental Health (NIMH) and National Alliance for the Mentally Ill (NAMI) brochure. Understanding Major Depression.

*Primary Examiner*—Mark L. Berch
*Assistant Examiner*—Kahsay Habte
(74) *Attorney, Agent, or Firm*—The Firm of Hueschen and Sage

(57) ABSTRACT

The invention relates to compound of formula (I):

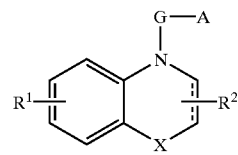

wherein:

G represents an alkylene chain containing from 1 to 4 carbon atoms,

A represents

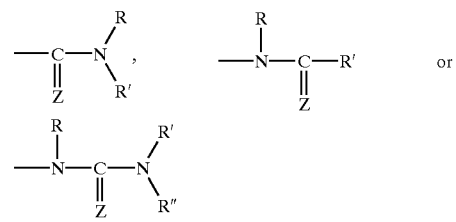

X represents oxygen or sulphur and $R^2$ and $R^1$ are as defined in the description and medicinal products containing the same which are useful in treating or in preventing melatoninergic disorders.

13 Claims, No Drawings

SUBSTITUTED (DIHYDRO)BENZOXAZINE AND (DIHYDRO)BENZOTHIAZINE COMPOUNDS

FIELD OF THE INVENTION

The present invention relates to new substituted (dihydro) benzoxazine and (dihydro) benzothiazine compounds that exhibit very valuable pharmacological properties in relation to melatoninergic receptors.

1. Description of the Prior Art

There may be found in the literature numerous substituted benzoxazine and benzothiazine structures for use both in synthesis (Tetrahedron, 53 (26), 1997, pp. 8853–8870; Heterocycl. Commun., 2 (3), 1996, pp. 273–274; J. Chem. Soc., Perkin Trans. 1, (10), 1991, pp. 2525–2529; Chem. Pharm. Bull., 34 (1), 1986, pp. 130–139; Indian J. Pharm., 35 (2), 1973, pp. 58–59) and as modulators of potassium channels (Eur J. Med. Chem., 33 (12), 1998, pp. 957–967; Chem. Pharm. Bull., 44 (1), 1996, pp. 103–114), or also as anti-cancer agents (Heterocycl. Commun., 3 (3), 1997, pp. 279–284; Heterocycl. Commun., 2 (6), 1996, pp. 587–592; Anti-Cancer Drugs, 6 (5), 1995, pp. 693–696).

2. Background of the Invention

Numerous studies in the last ten years have demonstrated the key role of melatonin (N-acetyl-5-methoxytryptamine) in many physiopathological phenomena and in the control of the circadian rhythm. Its half-life is quite short, however, owing to the fact that it is rapidly metabolised. Great interest therefore lies in the possiblity of providing the clinician with melatonin analogues that are metabolically more stable and have an agonist or antagonist character and that may be expected to have a therapeutic effect that is superior to that of the hormone itself.

In addition to their beneficial action on circadian rhythm disorders (J. Neurosurg. 1985, 63, pp. 321–341) and sleep disorders (Psychopharmacology, 1990, 100, pp. 222–226), ligands of the melatoninergic system have valuable pharmacological properties in respect of the central nervous system, especially anxiolytic and antipsychotic properties (Neuropharmacology of Pineal Secretions, 1990, 8 (3–4), pp. 264–272) and analgesic properties (Pharmacopsychiat., 1987, 20, pp. 222–223) as well as for the treatment of Parkinson's disease (J. Neurosurg. 1985, 63, pp. 321–341) and Alzheimer's disease (Brain Research, 1990, 528, pp. 170–174). Those compounds have also demonstrated activity in relation to certain cancers (Melatonin—Clinical Perspectives, Oxford University Press, 1988, pp. 164–165), ovulation (Science 1987, 227, pp. 714–720), diabetes (Clinical Endocrinology, 1986, 24, pp. 359–364), and in the treatment of obesity (International Journal of Eating Disorders, 1996, 20 (4), pp. 443–446).

Those various effects are exerted via the intermediary of specific melatonin receptors. Molecular biology studies have demonstrated the existence of a number of receptor subtypes that are capable of binding that hormone (Trends Pharmacol. Sci., 1995, 16, p 50; WO 97.04094). It has been possible, for various species, including mammals, for some of those receptors to be located and characterised. In order to be able to understand the physiological functions of those receptors better, it is of great advantage to have specific ligands available. Moreover, such compounds, by interacting selectively with one or other of those receptors, may be excellent medicaments for the clinician in the treatment of pathologies associated with the melatoninergic system, some of which have been mentioned above.

In addition to the fact that the compounds of the present invention are new, they show very strong affinity for melatonin receptors and/or selectivity for one or other of the melatoninergic binding sites.

DETAILED DESCRIPTION OF THE INVENTION

The present invention relates more especially to the compounds of formula (I):

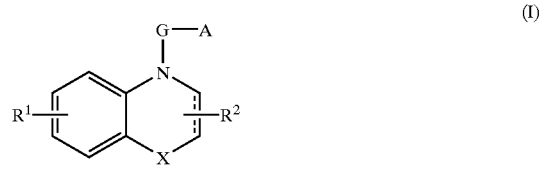

wherein:

$R^1$ represents a halogen atom or a group R, OR, SR, $SO_2NRR'$, —NRR',

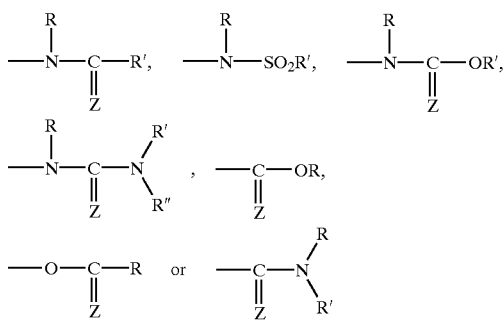

(wherein Z represent a sulpur atom or an oxygen atom and R, R' and R", which are identical or different, represent a hydrogen atom or an unsubstituted or substituted, linear or branched ($C_1$–$C_6$)alkyl group, an unsubstituted or substituted, linear or branched ($C_2$–$C_6$)alkenyl group, an unsubstituted or substituted, linear or branched ($C_2$–$C_6$) alkynyl group, an unsubstituted or substituted ($C_3$–$C_8$)- cycloalkyl group, an unsubstituted or substituted ($C_3$–$C_8$) cycloalkyl-($C_1$–$C_6$)alkyl group in which alkyl is linear or branched, an aryl group, an aryl($C_1$–$C_6$)alkyl group in which alkyl is linear or branched, a heteroaryl group or a heteroaryl-($C_1$–$C_6$)alkyl group in which alkyl is linear or branched, and wherein (R and R') or (R' and R") may together form, with the nitrogen atom carrying them, a morpholinyl, piperidinyl, piperazinyl or pyrrolidinyl group), G represents an alkylene chain containing from 2 to 4 carbon atoms when A represents a group

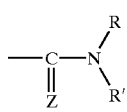

and from 1 to 4 carbon atoms in all other cases, G being optionally substituted by a group R, OR, COR or COOR (wherein R is as defined hereinbefore), A represents a group

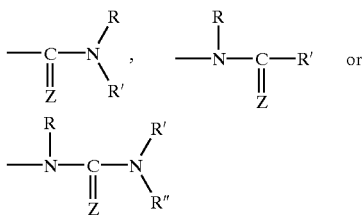

(wherein R, R' R" and Z are as defined hereinbefore), $R^2$ represents a halogen atom or a group R, OR, COR, COOR or OCOR (wherein R is as defined hereinbefore), X represents an oxygen atom or a sulphur atom, the symbol ==== denotes that the bond is single or double, the valency of the atoms being respected, wherein:

the term "substituted" applied to "alkyl", "alkenyl", "alkynyl" or "cycloalkyl" denotes that those groups may be substituted by one or more identical or different groups selected from hydroxy, alkoxy, alkyl, polyhaloalkyl, amino (unsubstituted or substituted by one or two linear or branched $(C_1-C_6)$alkyl groups) and halogen atoms, the term "substituted" applied to "cycloalkylalkyl" denotes that the cyclic moiety of the group is substituted by one or more identical or different groups selected from hydroxy, alkoxy, alkyl, polyhaloalkyl, amino (unsubstituted or substituted by one or two linear or branched $(C_1-C_6)$alkyl groups) and halogen atoms, "aryl" denotes a phenyl, naphthyl or biphenyl group, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido and halogen atoms, "heteroaryl" denotes any mono- or bi-cyclic aromatic group containing from one to three hetero atoms selected from oxygen, sulphur and nitrogen, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, amido and halogen atoms, to their enantiomers and diastereoisomers, and also to addition salts thereof with a pharmaceutically acceptable acid or base.

Amongst the pharmaceutically acceptable acids there may be mentioned, without implying any limitation, hydrochloric, hydrobromic, sulphuric, phosphonic, acetic, trifluoroacetic, lactic, pyruvic, malonic, succinic, glutaric, fumaric, tartaric, maleic, citric, ascorbic, methanesulphonic, camphoric, oxalic acid, etc.

Amongs the pharmaceutically acceptable bases there may be mentioned, without implying any limitation, sodium hydroxide, potassium hydroxide, triethylamine, tert-butylamine etc.

Preferred compounds of the invention are the compounds of formula (I) wherein X represents an oxygen atom.

The invention relates more especially to the benzoxazine compounds, and more preferably to the dihydrobenzoxazine compounds.

Preferred substituents $R^1$ are the groups alkyl, alkoxy and hydroxy.

Preferred substituents $R^2$ are the hydrogen atom and the groups aryl, heteroaryl, arylalkyl and heteroarylalkyl, and more especially the unsubstituted or substituted phenyl group.

Advantageously, the invention relates to the compounds of formula (I) wherein G represents a $(CH_2)_n$ chain in which n is 2 or 3.

Preferred substituents A are the groups NHCOR and CONHR.

The invention relates even more especially to the following compounds of formula (I):

N-[2-(6-hydroxy-2,3-dihydro-4H-1,4-benzoxazin-4-yl) ethyl]acetamide,

N-[2-(6-methoxy-2,3-dihydro-4H-1,4-benzoxazin-4-yl) ethyl]acetamide,

N-[2-(6-methoxy-2,3-dihydro-4H-1,4-benzoxazin-4-yl) ethyl]butanamide,

N-[2-(6-methoxy-2,3-dihydro-4H-1,4-benzoxazin-4-yl) ethyl]-3-butenamide,

N-[2-(6-methoxy-2,3-dihydro-4H-1,4-benzoxazin-4-yl) ethyl]cyclopropanecarboxamide, N-[2-(6-methoxy-2,3-dihydro-4H-1,4-benzoxazin-4-yl) ethyl]-2-furamide, N-[2-(6-methoxy-2,3-dihydro-4H-1,4-benzoxazin-4-yl) ethyl]benzamide, N[2-(6-hydroxy-2,3-dihydro-4H-1,4-benzoxazin-4-yl) ethyl]-2-furamide, N-[2-(6-methoxy-3-phenyl-2,3-dihydro-4H-1,4-benzoxazin-4-yl)ethyl]acetamide, N-[2-(6-methoxy-3-phenyl-2,3-dihydro-4H-1,4-benzoxazin-4-yl)ethyl]benzamide, N-[2-(6-methoxy-3-phenyl-2,3-dihydro-4H-1,4-benzoxazin-4-yl)ethyl]-2-furamide, N-[2-(6-methoxy-3-phenyl-2,3-dihydro-4H-1,4-benzoxazin-4-yl)ethyl]butanamide, N-[2-(6-methoxy-2-phenyl-2,3-dihydro-4H-1,4-benzoxazin-4-yl)ethyl]acetamide, N-[2-(6-methoxy-2-phenyl-2,3-dihydro-4H-1,4-benzoxazin-4-yl)ethyl]-2-furamide, N-[2-(6-methoxy-2-phenyl-2,3-dihydro-4H-1,4-benzoxazin-4-yl)ethyl]benzamide, N-[2-(6-methoxy-2-phenyl-2,3-dihydro-4H-1,4-benzoxazin-4-yl)ethyl]butanamide, N-[2-(6-methoxy-2-phenyl-2,3-dihydro-4H-1,4-benzoxazin-4-yl)ethyl]cyclopropanecarboxamide.

The enantiomers, diastereoisomers and also the addition salts with a pharmaceutically acceptable acid or base of the preferred compounds of the invention form an integral part of the invention.

The invention extends also to a process for the preparation of the compounds of formula (I) which is characterised in that there is used as starting material a compound of formula (II):

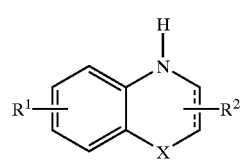

wherein $R^1$, $R^2$, X and the symbol ==== are as defined in formula (I), with which there is reacted, in basic medium, a compound of formula (III)

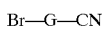     (III)

wherein G is as defined in formula (I), to yield a compound of formula (IV):

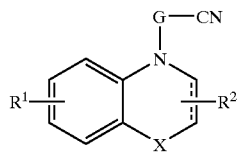     (IV)

wherein $R^1$, $R^2$, X, G and the symbol === are as defined hereinbefore, which is subjected to hydrolysis, under acid or basic conditions, to yield a compound of formula (V):

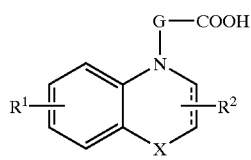     (V)

wherein $R^1$, $R^2$, X, G and the symbol === have the same definitions as hereinbefore, which is acted upon, in the presence of a coupling agent or after conversion into the corresponding acid chloride, by an amine HNRR' wherein R and R' are as defined in formula (I), to yield a compound of formula (I/a), a particular case of the compounds of formula (I):

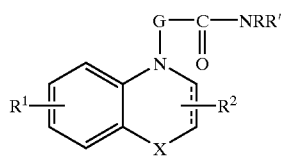     (I/a)

wherein $R^1$, $R^2$, X, G, R, R' and the symbol === are as defined hereinbefore, which compound of formula (I/a) is subjected, when R and R' simultaneously represent a hydrogen atom, to the action of NaOBr to yield, after hydrolysis, a compound of formula (VI):

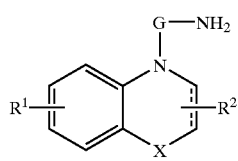     (VI)

wherein $R^1$, $R^2$, X, G and the symbol === are as defined hereinbefore, which compounds of formula (VI) (which furthermore can be obtained by reduction of the compound of formula (IV)) are subjected to the action:

of an acyl chloride of formula (VII):

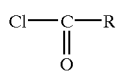     (VII)

wherein R is as defined hereinbefore, or to a corresponding (mixed or symmetrical) acid anhydride, to obtain a compound of formula (I/b), a particular case of the compounds of formula (I):

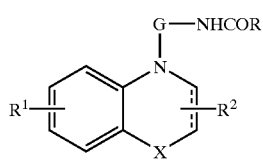     (I/b)

wherein $R^1$, $R^2$, R, X, G and the symbol === have the same definitions as hereinbefore, or of a compound of formula (VIII):

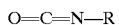     (VIII)

wherein R is as defined hereinbefore, to yield a compound of formula (I/c), a particular case of the compounds of formula (I):

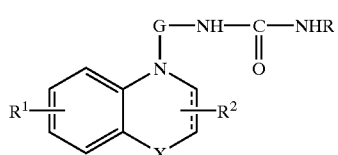     (I/c)

wherein $R^1$, $R^2$, R, X, G and the symbol === are as defined hereinbefore, wherein the compounds of formulae (I/b) and (I/c) may be subjected to the action of a compound of formula (IX):

     (IX)

wherein $R_a$ may have any of the meanings of R with the exception of a hydrogen atom and J represents a leaving group, such as a halogen atom or a tosyl group, to yield a compound of formula (I/d), a particular case of the compounds of formula (I):

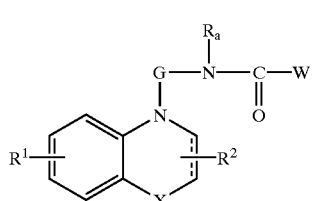     (I/d)

wherein $R^1$, $R^2$, X, G, $R_a$ and the symbol === have the same definitions as hereinbefore and W represents a group R or —NRR' wherein R and R' are as defined hereinbefore, and/or the compounds of formulae (I/a), (I/b), (I/c) and (I/d) may be subjected to the action of a thionisation agent, such as Lawesson's reagent, to yield a compound of formula (I/e), a particular case of the compounds of formula (I):

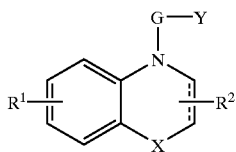
(I/e)

wherein $R^1$, $R^2$, X, G and the symbol === are as defined hereinbefore and Y represents a group

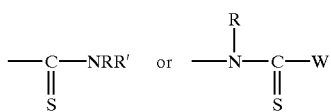

wherein R, R' and W are as defined hereinbefore, the compounds (I/a) to (I/e) constituting the totality of the compounds of formula (I) and wherein those compounds may be purified according to a conventional separation technique, may be converted, if desired, into their addition salts with a pharmaceutically acceptable acid or base, and may optionally be separated into their isomers according to a conventional separation technique.

The compounds of formula (II) are either commercially available, or accessible to the person skilled in the art by conventional chemical reactions.

In particular, the compounds of formula (II) can be obtained starting from compounds of formula (X):

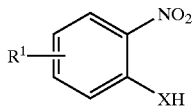
(X)

wherein $R^1$ and X are as defined hereinbefore, which are subjected to catalytic hydrogenation to obtain a compound of formula (XI):

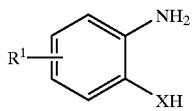
(XI)

wherein $R^1$ and X are as defined hereinbefore, which is acetylated to yield a compound of formula (XII):

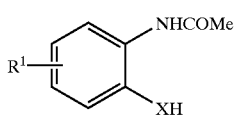
(XII)

wherein $R^1$ and X are as defined hereinbefore, which is acted upon by a compound of formula (XIII):

(XIII)

wherein Hal represents a halogen atom and $R^2$ is as defined hereinbefore, to yield a compound of formula (XIV):

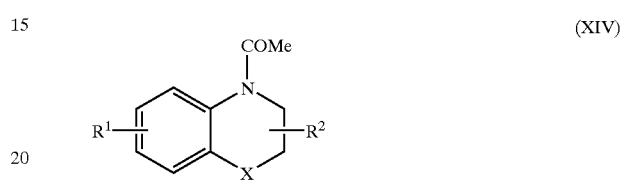
(XIV)

wherein $R^1$, $R^2$ and X are as defined hereinbefore, which is hydrolysed in basic medium to obtain a compound of formula (XV), a particular case of the compounds of formula (II):

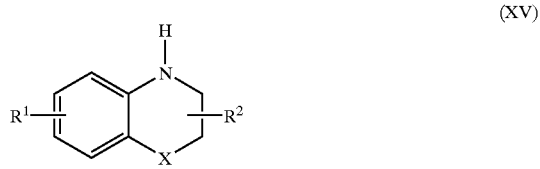
(XV)

wherein $R^1$, $R^2$ and X are as defined hereinbefore, it being equally possible for a compound of formula (XV) to be obtained starting from a compound of formula (X), which is subjected to the action of a compound of formula (XVI):

(XVI)

wherein Hal represents a halogen atom and $R^2$ is as defined hereinbefore, to yield a compound of formula (XVII):

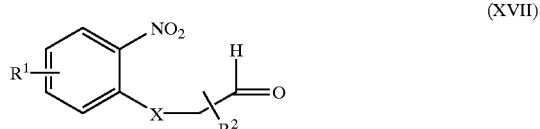
(XVII)

wherein $R^1$, X and $R^2$ are as defined hereinbefore, which is subjected to catalytic hydrogenation to yield a compound of formula (XV), a particular case of the compounds of formula (II), it being possible, moreover, for a compound of formula (XV) in which the group $R^2$ is in the ortho position to X to be obtained starting from a compound of formula (XI), which is subjected to the action of a compound of formula (XVIII):

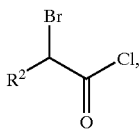
(XVIII)

wherein R² is as defined hereinbefore, in basic medium, then to the action of K₂CO₃, to yield a compound of formula (XIX):

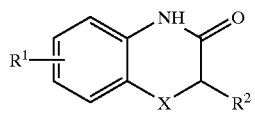
(XIX)

wherein R¹, R² and X are as defined hereinbefore, which is subjected to the action of a reducing agent, such as LiAlH₄ for example, to obtain a compound of formula (XV'), a particular case of the compounds of formula (XV):

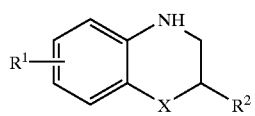
(XV')

wherein R¹, R² and X are as defined hereinbefore, wherein the compound of formula (XV) may be subjected to the conditions of oxidation to yield a compound of formula (XX), a particular case of the compounds of formula (II):

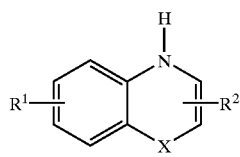
(XX)

wherein R¹, R² and X are as defined hereinbefore.

The compounds of the invention and the pharmaceutical compositions containing them prove to be useful in the treatment of disorders of the melatoninergic system.

Pharmacological study of the compounds of the invention has in fact shown that they are atoxic, have a very high selective affinity for melatonin receptors and have substantial activities in respect of the central nervous system, and, in particular, therapeutic properties in respect of sleep disorders, anxiolytic, antipsychotic and analgesic properties, as well as properties in respect of microcirculation have been found, enabling it to be established that the compounds of the invention are useful in the treatment of stress, sleep disorders, anxiety, seasonal affective disorder, cardiovascular pathologies, pathologies of the digestive system, insomnia and fatigue caused by jetlag, schizophrenia, panic attacks, melancholia, appetite disorders, obesity, insomnia, psychotic disorders, epilepsy, diabetes, Parkinson's disease, senile dementia, various disorders associated with normal or pathological ageing, migraine, memory loss, Alzheimer's disease, and in cerebral circulation disorders. In another field of activity, it appears that the compounds of the invention can be used in the treatment of sexual dysfunctions, that they have ovulation-inhibiting and immunomodulating properties and that they are capable of being used in the treatment of cancers.

The compounds will preferably be used in the treatment of seasonal affective disorder, sleep disorders, cardiovascular pathologies, insomnia and fatigue caused by jet-lag, appetite disorders and obesity.

For example, the compounds will be used in the treatment of seasonal affective disorder and sleep disorders.

The present invention relates also to pharmaceutical compositions comprising at least one compound of formula (I), on its own or in combination with one or more pharmaceutically acceptable excipients.

Amongst the pharmaceutical compositions according to the invention there may be mentioned more especially those which are suitable for oral, parenteral, nasal, percutaneous, transcutaneous, rectal, perlingual, ocular or respiratory administration, and especially tablets or dragées, sublingual tablets, sachets, paquets, gelatin capsules, glossettes, lozenges, suppositories, creams, ointments, dermal gels, and injectable or drinkable ampoules.

The dosage varies in accordance with the sex, age and weight of the patient, the administration route, the nature of the therapeutic indication, or possibly associated treatments, and ranges from 0.01 mg to 1 g per 24 hours in one or more administrations.

The following Examples illustrate the invention and do not limit it in any way. The following preparations yield synthesis intermediates useful in the preparation of the compounds of the invention.

EXAMPLE 1

N-[2-(6-Methoxy-2,3-dihydro-4H-1,4-benzoxazin-4-yl)ethyl]-acetamide

Step A: 1-Amino-4-methoxyphenol

4-Methoxy-2-nitrophenol (5 g; 29.56 mmol) is dissolved in methanol. Palladium-on-carbon (5% by weight, 250 mg) is then added. The mixture is stirred in a Parr apparatus for 1 hour under 40 psi of hydrogen. The solution is subsequently filtered over Celite, and the solvent is then removed under reduced pressure to yield the title product in the form of a black solid having a metallic gleam.

Melting point: 138–140° C.

Step B N-(2-Hydroxy-5-methoxyphenyl)acetamide

The compound obtained in Step A (1 g; 7.19 mmol) is dissolved in 16 ml of water with the aid of concentrated hydrochloric acid (0.58 ml). Acetic anhydride (1.2 eq.; 8.62 mmol; 813 μl) is added to the red solution obtained. The mixture is homogenised and poured into 5 ml of a sodium acetate solution (1.7 eq.; 12.22 mmol; 1.075 g). After stirring the mixture for 15 minutes, the precipitate is filtered off using a Büchner funnel and then rinsed with water. The solid is subsequently dissolved in ethyl acetate and then dried over MgSO₄. After filtration, the solvent is removed under reduced pressure to yield the title product in the form of a red solid.

Melting point: 156–157° C.

Step C: 1-(6-Methoxy-2,3-dihydro-4H-1,4-benzoxazin-4-yl)-1-ethanone

Under anhydrous conditions, the compound obtained in Step B (1 g; 5.52 mmol) is dissolved in an acetonitrile/dichloromethane mixture (4/6). Sodium hydroxide (4 eq.; 22.1 mmol; 883 mg) that has been ground beforehand, dibromoethane (4 eq.; 22.1 mmol; 1.96 mmol) and Aliquat 336 (catalytic amount) are added to the solution. The whole is stirred for 24 hours at 30° C., under argon, and then 220 mg (1 eq.) of sodium hydroxide are added to terminate the reaction. The solution is filtered through fritted glass, and the brown solid is rinsed with ether. The red filtrate is recovered, and the solvents are removed under reduced pressure. The residue obtained is purified by flash chromatography on silica gel (eluant: PE/AcOEt (1/1)). The title product is obtained in the form of a red solid.

Melting point: 76–77° C.

Step D: 6-Methoxy-3,4-dihydro-2H-1,4-benzoxazine

The compound obtained in Step C (1.5 g; 7.26 mmol) is dissolved in 7 ml of methanol, and then water (14 eq.; 101.6 mmol; 1.9 ml) and potassium hydroxide (6 eq.; 43.5 mmol; 2.44 g) are added. The solution is stirred vigorously at 60° C. for 2 hours. After extraction three times with dichloromethane, the organic phase is dried over $MgSO_4$ and then removed under reduced pressure. The residue obained is purified by flash chromatography on silica gel (eluant: PE/AcOEt (1/1)). The title product is obtained in the form of a red solid.

Melting point: 59–61° C.

{or Step A': 6-Methoxy-2H-1,4-benzoxazin-3-one

The compound obtained in Step A (5.94 g; 42.7 mmol) is dissolved in 50 ml of methyl isobutyl ketone, and a solution of sodium hydrogen carbonate (3 eq.; 128.1 mmol; 10.76 g dissolved in 60 ml of water) is subsequently added. Chloroacetyl chloride (1.1 eq.; 46.9 mmol; 3.74 ml) is then slowly added. The mixture is maintained at reflux for one hour, then the methyl isobutyl ketone is removed under reduced pressure. The residue is taken up in ethyl acetate, and the organic phase is washed twice with water, dried over $MgSO_4$, and subsequently removed under reduced pressure to yield the title product in the form of a solid.

Step D: 6-Methoxy-3,4-dihydro-2H-1,4-benzoxazine

Under an inert atmosphere, the compound obtained in Step A' (2.1 g; 11.7 mmol) is dissolved in 60 ml of tetrahydrofuran, then lithium aluminium hydride (5.5 eq.; 2.45 g; 64.5 mmol) is added in portions. The mixture is stirred for 24 hours at ambient temperature. The temperature of the solution is lowered to 0° C., and then 2.45 ml of water, 2.45 ml of 15% sodium hydroxide and 7.35 ml of water are slowly added. The mixture is stirred for 30 minutes and then filtered using a Büchner funnel. After removal of the solvents under reduced pressure, the residue obtained is purified by flash chromatography on silica gel (eluant: PE/AcOEt (6/4)). The title product is obtained in the form of a red solid.

Melting point: 59–61° C.}

Step E: 2-(6-Methoxy-2,3-dihydro-4H-1,4-benzoxazin-4-yl)acetonitrile

The compound obtained in Step D (400 mg; 2.42 mmol) is suspended in 10 ml of water. Potassium carbonate (10 eq.; 24.2 mmol; 3.35 g), tetrabutylammonium bromide (0.05 eq.; 0.12 mmol; 40 mg) and bromoacetonitrile (8 eq.; 19.37 mmol; 1.35 ml) are then added. The mixture is stirred vigorously for 12 hours at 70° C. After returning to ambient temperature, the product formed is extracted with dichloromethane. The organic phase is dried over $MgSO_4$, filtered, and then concentrated under reduced pressure. The residue obained is purified by flash chromatography on silica gel (eluant: PE/AcOEt (1/1)). The title product is obtained in the form of a solid.

Melting point: 73–74° C.

Step F: N-[2-(6-Methoxy-2,3-dihydro-4H-1,4-benzoxazin-4-yl)ethyl]acetamide

The compound obtained in Step E (590 mg; 2.88 mmol) is dissolved in a Parr reactor with acetic anhydride. Raney nickel (10% by weight, 60 mg) and sodium acetate (1.5 eq.; 4.33 mmol; 355 mg) are then added. The mixture is left for 12 hours at 50° C. under a hydrogen pressure of 40 psi. After returning to ambient temperature, the solution is filtered over Celite and the filtrate is evaporated. The residue obtained is taken up in water and then extracted three times with ethyl acetate. The organic phases are combined, dried over $MgSO_4$, and then concentrated under reduced pressure. The crude reaction product is purified by flash chromatography on silica gel (eluant: PE/AcOEt (4/6) then AcOEt/MeOH (95/5)). The title product is obtained in the form of white crystals after washing with ether.

Melting point: 107–108° C.

| Elemental microanalysis: | | | |
|---|---|---|---|
| | C % | H % | N % |
| Calculated: | 62.38 | 7.25 | 11.19 |
| Found: | 62.26 | 7.60 | 11.05 |

EXAMPLE 2

N-[2-(6-Methoxy-2,3-dihydro-4H-1,4-benzoxazin-4-yl)ethyl]-butanamide

Under an inert atmosphere, the compound obtained in Step E of Example 1 is dissolved in anhydrous ether (1 ml/0.1 mmol) and then lithium aluminium hydride (1.5 eq.) is added in portions. The mixture is stirred at ambient temperature for 3 hours, and then the solution is hydrolysed with water and 15% sodium hydroxide. The solution is stirred for 30 minutes, and then the salts that have formed are filtered off using a Büchner funnel. The solvents are removed under reduced pressure, and the yellow oil obtained is placed under a dynamic vacuum under $P_2O_5$ for 2 hours. Without further purification, the amine obtained is used directly in the acylation reaction.

Under an inert atmosphere, the amine is dissolved in distilled dichloromethane, and then the solution is cooled to 0° C. Triethylamine (3 eq.), and then butyryl chloride (1.5 eq.), are slowly added. The mixture is left at ambient temperature until the amine has disappeared, and then the organic phase is washed with water and dried over $MgSO_4$ and the solvents are removed under reduced pressure. The residue obtained is purified by flash chromatography on silica gel (eluant: PE/AcOEt (2/8)) to obtain the title product in the form of a solid, which is recrystallised from ether.

Melting point: 73–74° C.

| Elemental microanalysis: | | | |
|---|---|---|---|
| | C % | H % | N % |
| Calculated: | 64.73 | 7.97 | 10.06 |
| Found: | 64.57 | 8.02 | 10.10 |

EXAMPLE 3

N-[2-(6-Methoxy-2,3-dihydro-4H-1,4-benzoxazin-4-yl)ethyl]-3-butenamide

Under an inert atmosphere, the compound obtained in Step E of Example 1 (294 mg; 1.44 mmol) is dissolved in 14 ml of anhydrous ether, and then lithium aluminium hydride (1.5 eq.; 2.16 mmol; 82 mg) is added in portions. The mixture is stirred at ambient temperature for 3 hours, and then the solution is hydrolysed with 82 µl of water, 82 µl of a 15% sodium hydroxide solution and 246 µl of water. The solution is stirred for 30 minutes, then the salts that have formed are filtered off using a Büchner funnel. The solvents are removed under reduced pressure, and the yellow oil obtained is used directly in the subsequent reaction.

Under an inert atmosphere at −10° C., vinylacetic acid (1.5 eq.; 2.16 mmol; 190 µl) diluted with 7 ml of distilled dichloromethane is placed in the presence of EDCI (1.5 eq.; 2.16 mmol; 422 mg) and HOBt (1.5 eq.; 2.16 mmol; 292 mg). The whole is stirred under argon at −10° C. for 30 minutes. In parallel, the amine is dissolved in 10 ml of distilled dichloromethane and placed in the presence of triethylamine (1 eq.; 1.44 mmol; 200 µl). The activated vinylacetic acid is then added to the solution of free amine. The reaction mixture is left for one hour at −10° C. and then for 24 hours at ambient temperature. The mixture is subsequently washed with a 1N sodium hydroxide solution, and water, and dried over $MgSO_4$, and the solvent is evaporated off under reduced pressure. The residue obtained is purified by flash chromatography (eluant: PE/AcOEt (3/7)). The title product is obtained in the form of a solid, which is recrystallised from an $Et_2O$/i-PrOH mixture.

Melting point: 80–81° C.

| | Elemental microanalysis: | | |
|---|---|---|---|
| | C % | H % | N % |
| Calculated: | 65.20 | 7.29 | 10.14 |
| Found: | 64.55 | 7.35 | 9.93 |

EXAMPLE 4

N-[2-(6-Methoxy-2,3-dihydro-4H-1,4-benzoxazin-4-yl)ethyl]cyclo-propanecarboxamide The procedure is as in Example 2, with the replacement of butyryl chloride with cyclopropanecarbonyl chloride. Recrystallisation from $Et_2O$/iPrOH (99/1).

Melting point: 121–122° C.

| | Elemental microanalysis: | | |
|---|---|---|---|
| | C % | H % | N % |
| Calculated: | 65.20 | 7.29 | 10.14 |
| Found: | 65.04 | 7.36 | 9.88 |

EXAMPLE 5

N-[2-(6-Methoxy-2,3-dihydro-4H-1,4-benzoxazin4-yl)ethyl]-2-furamide

The procedure is as in Example 2, with the replacement of butyryl chloride with 2-furoyl chloride. Recrystallisation from $Et_2O$.

Melting point: 95–96° C.

| | Elemental microanalysis: | | |
|---|---|---|---|
| | C % | H % | N % |
| Calculated: | 63.57 | 6.00 | 9.27 |
| Found: | 63.47 | 6.05 | 9.11 |

EXAMPLE 6

N-[2-(6-Methoxy-2,3-dihydro-4H-1,4-benzoxazin-4-yl)ethyl]-benzamide

The procedure is as in Example 2, with the replacement of butyryl chloride with benzoyl chloride. Recrystallisation from $Et_2O$/iPrOH.

Melting point: 114–117° C.

| | Elemental microanalysis: | | |
|---|---|---|---|
| | C % | H % | N % |
| Calculated: | 69.21 | 6.45 | 8.97 |
| Found: | 68.78 | 6.60 | 8.86 |

EXAMPLE 7

N-[2-(6-Hydroxy-2,3-dihydro-4H-1,4-benzoxazin-4-yl)ethyl]-acetamide

Under argon, the compound obtained in Example 1 (342 mg; 1.37 mmol) is dissolved in 8 ml of distilled dichloromethane. The solution is cooled to −78° C., and then boron tribromide (4 eq.; 5.47 mmol; 5.17 µl) diluted with 5 ml of dichloromethane is slowly added. The mixture is left for one hour at −78° C. and then for 2 hours at ambient temperature. The reaction mixture is hydrolysed to pH 7 with a saturated sodium hydrogen carbonate solution and then the aqueous phase is extracted 4 times with dichloromethane. The organic phases are combined, and then removed under reduced pressure. The solid obtained is dissolved in a minimum amount of dichloromethane, precipitated in the presence of pentane, filtered, and then washed with an $Et_2O$/pentane mixture.

Melting point: 179–181° C.

| | Elemental microanalysis: | | |
|---|---|---|---|
| | C % | H % | N % |
| Calculated: | 61.00 | 6.83 | 11.86 |
| Found: | 60.49 | 6.87 | 11.86 |

EXAMPLE 8

N-[2-(6-Hydroxy-2,3-dihydro-4H-1,4-benzoxazin-4-yl)ethyl]-2-furamide

Under argon, the compound obtained in Example 5 (245 mg; 0.1 mmol) is dissolved in 8 ml of distilled dichloromethane. The solution is cooled to −78° C., and then boron tribromide (4 eq.; 3.25 mmol; 307 µl) diluted with 5 ml of dichloromethane is slowly added. The mixture is left for 1 hour at −78° C. and then for 2 hours at ambient temperature. The reaction mixture is hydrolysed to pH 7 with a saturated NaHCO$_3$ solution, and then the aqueous phase is extracted 4 times with dichloromethane. The organic phases are combined, dried over MgSO$_4$, and then concentrated under reduced pressure. The crude reaction product is purified by flash chromatography on silica gel (eluant: PE/AcOEt (1/1) then (1/9)). The title product is obtained in the form of a solid after trituration with pentane.

Melting point: 59–62° C.

| Elemental microanalysis: | | | |
| --- | --- | --- | --- |
|  | C % | H % | N % |
| Calculated: | 62.49 | 5.59 | 9.72 |
| Found: | 63.18 | 5.65 | 9.33 |

EXAMPLE 9

N-[2-(6-Ethyl-2,3-dihydro-4H-1,4-benzoxazin-4-yl)ethyl]acetamide

The procedure is as in Example 1, starting from 4-ethyl-2-nitrophenol.

EXAMPLE 10

N-[2-(6-Methoxy-2,3-dihydro-4H-1,4-benzothiazin-4-yl)-ethyl]acetamide

The procedure is as in Example 1, starting from 4-methoxy-2-nitrobenzenethiol.

EXAMPLE 11

N-[2-(6-Methoxy-2,3-dihydro-4H-1,4-benzothiazin-4-yl)ethyl]-2-phenylacetamide

The procedure is as in Example 2, starting from 4-methoxy-2-nitrobenzenethiol and with the replacement of butyryl chloride with 2-phenylacetyl chloride.

EXAMPLE 12

4-(6-Methoxy-2,3-dihydro-4H-1,4-benzoxazin-4-yl)-N-methyl-butanamide

Step A: 3-(6-Methoxy-2,3-dihydro-4H-1,4-benzoxazin-4-yl)butanenitrile

The procedure is as in Step E of Example 1, with the replacement of bromoacetonitrile with 4-bromobutanenitrile.

Step B: 4-(6-Methoxy-2,3-dihydro-4H-1,4-benzoxazin-4-yl)butanoic acid

The compound obtained in Step A is hydrolysed in the presence of NaOH.

Step C: 4-(6-Methoxy-2,3-dihydro-4H-1,4-benzoxazin-4-yl)-N-methylbutanamide

The acid obtained in Step B is subjected to the action of SOCl$_2$ to yield the intermediate acid chloride, which is condensed with N-methylamine to obtain the title product.

EXAMPLE 13

N-Cyclobutyl-4-(6-methoxy-2,3-dihydro-4H-1,4-benzoxazin-4-yl)-butanamide

The procedure is as in Example 12, with the replacement of N-methylamine with N-cyclobutylamine.

EXAMPLE 14

N-[2-(6-Methoxy-3-phenyl-2,3-dihydro-4H-1,4-benzoxazin-4-yl)-ethyl]acetamide

Step A: 2-(4-Methoxy-2-nitrophenoxy)-1-phenyl-1-ethanone

Under an inert atmosphere, 4-methoxy-2-nitrophenol (1.5 g; 8.86 mmol) is dissolved in 30 ml of acetone, and then 2-bromoacetophenone (1.5 eq.; 13.29 mmol; 2.79 g) and also potassium carbonate (1.2 eq.; 10.64 mmol; 1.47 g) are added. The mixture is stirred vigorously, at reflux, for 3 hours. After returning to ambient temperature, the potassium carbonate is filtered off, the filtrate is evaporated and the residue is taken up in a water/ethyl acetate mixture. The organic phase is dried over MgSO$_4$ and then concentrated under reduced pressure. The crude reaction product is purified by flash chromatography on silica gel (eluant: PE/AcOEt (8/2)). The title product is obtained in the form of a yellow solid.

Melting point: 88–90° C.

Step B: 6-Methoxy-3-phenyl-3,4-dihydro-2H-1,4-benzoxazine

The compound obtained in Step A (3 g; 10.44 mmol) is dissolved in a Parr reactor with an ethanol/tetrahydrofuran mixture (1/1). Raney nickel (30% by weight, 900 mg) is then added. The mixture is left for 48 hours at 50° C. under a hydrogen pressure of 50 psi. After returning to ambient temperature, the solution is filtered over Celite and the filtrate is evaporated. The crude reaction product is purified by flash chromatography on silica gel (eluant: PE/AcOEt (85/15)). The title product is obtained in the form of a yellow solid.

Melting point: 79–81° C.

Step C: 2-(6-Methoxy-3-phenyl-2,3-dihydro-4H-1,4-benzoxazin-4-yl)acetonitrile

The compound obtained in Step B (480 mg; 1.99 mmol) is suspended in 8 ml of water (4 ml/1 mmol). Potassium hydrogen carbonate (10 eq.; 19.89 mmol; 1.657 g), tetrabutylammonium bromide (1 eq.; 1.99 mmol; 641 mg) and bromoacetonitrile (8 eq.; 15.91 mmol; 1.11 ml) are then added. The mixture is stirred vigorously at 90° C. for 8 hours. After returning to ambient temperature, the product formed is extracted with dichloromethane. The organic phase is dried over MgSO$_4$, filtered, and then concentrated under reduced pressure. The residue obtained is purified by flash chromatography on silica gel (eluant: PE/AcOEt (8/2)). The title product is obtained in the form of a colourless oil.

Step D: N-[2-(6-Methoxy-3-phenyl-2,3-dihydro-4H-1,4-benzoxazin-4-yl)ethyl]-acetamide The compound obtained in Step C (200 mg; 0.71 mmol) is dissolved in a Parr reactor with acetic anhydride. Raney nickel (30% by weight, 60 mg) and sodium acetate (1.5 eq.; 1.07 mmol; 88 mg) are then added. The mixture is left at 50° C. for 36 hours under a hydrogen pressure of 40 psi. After returning to ambient temperature, the solution is filtered over Celite and the filtrate is evaporated. The crude reaction product is purified by flash chromatography on silica gel (eluant: AcOEt). The title product is obtained in the form of white crystals, which are recrystallised from an Et₂O/i-PrOH mixture.
Melting point: 125–126° C.

Elemental microanalysis:

|  | C % | H % | N % |
|---|---|---|---|
| Calculated: | 69.92 | 6.79 | 8.58 |
| Found: | 70.00 | 6.95 | 8.50 |

EXAMPLE 15

N-[2-(6-Methoxy-3-phenyl-2,3-dihydro-4H-1,4-benzoxazin-4-yl)-ethyl]benzamide

Under an inert atmosphere, the compound obtained in Step C of Example 14 is dissolved in anhydrous ether (1 ml/0.1 mmol), and lithium aluminium hydride (1.5 eq.) is then added in portions. The mixture is stirred at ambient temperature for 3 hours, and then the solution is hydrolysed, at 0° C., with water and a 15% sodium hydroxide solution. The solution is stirred for 30 minutes, and then the salts that have formed are filtered off using a Büchner funnel. The solvents are removed under reduced pressure, and the yellow oil obtained is placed under a dynamic vacuum under $P_2O_5$ for 2 hours. Without further purification, the amine obtained is used directly in the acylation reaction. Under an inert atmosphere, the amine is dissolved in distilled dichloromethane, and then the solution is cooled to 0° C. Triethylamine (3 eq.), and then benzoyl chloride (1.5 eq.), are slowly added. The mixture is left at ambient temperature until the amine has disappeared, and then the organic phase is washed with water and dried over $MgSO_4$ and the solvents are removed under reduced pressure. The residue obtained is purified by flash chromatography on silica gel (eluant PE/AcOEt (7/3) then (6/4)) to obtain an oil which yields a solid after crystallisation from $CH_2Cl_2$.
Melting point: 61–62° C.

Elemental microanalysis:

|  | C % | H % | N % |
|---|---|---|---|
| Calculated: | 74.21 | 6.23 | 7.21 |
| Found: | 73.86 | 6.25 | 7.11 |

EXAMPLE 16

N-[2-(6-Methoxy-3-phenyl-2,3-dihydro-4H-1,4-benzoxazin-4-yl) ethyl]-2-furamide

The procedure is as in Example 15, with the replacement of benzoyl chloride with 2-furoyl chloride.
Melting point: 52–54° C.

Elemental microanalysis:

|  | C % | H % | N % |
|---|---|---|---|
| Calculated: | 69.83 | 5.86 | 7.40 |
| Found: | 69.62 | 5.90 | 7.14 |

EXAMPLE 17

N-[2-(6-Methoxy-3-phenyl-2,3-dihydro-4H-1,4-benzoxazin-4-yl)ethyl]butanamide

The procedure is as in Example 15, with the replacement of benzoyl chloride with butyryl chloride.
Melting point: 60–62° C.

Elemental microanalysis:

|  | C % | H % | N % |
|---|---|---|---|
| Calculated: | 71.16 | 7.39 | 7.90 |
| Found: | 70.68 | 7.33 | 7.77 |

EXAMPLE 18

N-(2-{6-Methoxy-3-[3-(trifluoromethyl)phenyl]-2,3-dihydro-4H-1,4-benzoxazin-4-yl}ethyl) cyclopropanecarboxamide Step A: 2-{6-Methoxy-3-[3-(trifluoromethyl)phenyl]-2,3-dihydro-4H-1,4-benzoxazin-4-yl}acetonitrile The procedure is as in Steps A, B and C of Example 14, with the replacement of 2-bromoacetophenone with 2-bromo-1-[3-(trifluoromethyl)phenyl]-1-ethanone in Step A.

Step B: N-(2-{6-Methoxy-3-[3-(trifluoromethyl)phenyl]-2,3-dihydro-4H-1,4-benzoxazin-4-yl}ethyl) cyclopropanecarboxamide The procedure is as in Example 15, starting from the compound obtained in Step A and with the replacement of benzoyl chloride with cyclopropylcarbonyl chloride.

EXAMPLE 19

N-[-2-(3-Benzyl-6-methoxy-2,3-dihydro-4H-1,4-benzoxazin-4-yl)ethyl]acetamide

The procedure is as in Example 14, with the replacement of 2-bromoacetophenone with 1-bromo-3-phenylacetone in Step A.

EXAMPLE 20

2-Methyl-N-[2-(3-phenyl-2,3-dihydro-4H-1,4-benzothiazin-4-yl)ethyl]propanamide

Step A: 2-(3-Phenyl-2,3-dihydro-4H-1,4-benzothiazin-4-yl)acetonitrile

The procedure is as in Steps A, B and C of Example 14, starting from 4-methoxy-2-nitrobenzenethiol.

Step B: 2-Methyl-N-[2-(3-phenyl-2,3-dihydro-4H-1,4-benzothiazin-4-yl)ethyl]propanamide The procedure is as in Example 15, starting from the compound obtained in Step A and with the replacement of benzoyl chloride with isobutyryl chloride.

EXAMPLE 21

4-(6-Methoxy-3-phenyl-2,3-dihydro-4H-1,4-benzoxazin-4-yl)-N-methylbutanamide

Step A: 4-(6-Methoxy-3-phenyl-2,3-dihydro-4H-1,4-benzoxazin-4-yl)butanenitrile

The procedure is as in Steps A, B and C of Example 14, with the replacement of bromoacetonitrile with 4-bromobutanenitrile in Step C.

Step B: 4-(6-Methoxy-3-phenyl-2,3-dihydro-4H-1,4-benzoxazin-4-yl)-N-methylbutanamide The procedure is as in Steps B and C of Example 12.

EXAMPLE 22

N-Hexyl-4-(6-methoxy-3-phenyl-2,3-dihydro-4H-1,4-benzothiazin-4-yl)butanamide

The procedure is as in Example 21, with the replacement of N-methylamine with N-hexylamine.

EXAMPLE 23

N-[2-(6-Methoxy-2-phenyl-2,3-dihydro-4H-1,4-benzoxazin-4-yl)ethyl]acetamide

Step A: 2-Bromo-N-(2-hydroxy-5-methoxyphenyl)-2-phenylacetamide

2-Bromophenylacetyl chloride (1.2 eq.; 32.55 mmol; 7.60 g) is slowly added at 0° C., in the presence of 33 ml of water (1.2 ml/1 mmol) and sodium hydrogen carbonate (1.5 eq.; 40.7 mmol; 3.42 g), to a solution of the compound obtained in Step A of Example 1 (3.77 g; 27.13 mmol) dissolved in 33 ml of ethyl acetate (1.2 ml/1 mmol). The mixture is stirred for 2 hours. After the addition of ethyl acetate to the reaction mixture, the organic phase is washed once with water, dried over $MgSO_4$ and concentrated under reduced pressure. The crude reaction product is purified by flash chromatography on silica gel after solid deposit (eluant: PE/AcOEt (7/3) then (6/4)). The title product is obtained in the form of a maroon solid, which is recrystallised from an $Et_2O$/i-PrOH mixture.
Melting point: 145–147° C.

Step B: 6-Methoxy-2-phenyl-2H-1,4-benzoxazin-3(4H)-one

The compound obtained in Step A (5 g; 14.87 mmol) is dissolved in 15 ml of dimethylformamide (1 ml/1 mmol), and then potassium carbonate (1.5 eq.; 22.31 mmol; 3.08 g) is added. The solution is stirred at ambient temperature for 2.5 hours, and then 60 ml of water are added and a precipitate is formed. After one night in a refrigerator, the solid is filtered through fritted glass, rinsed with water, and dried under a dynamic vacuum under $P_2O_5$ to yield the title product, which is used in the subsequent reaction without being further purified.

Step C: 6-Methoxy-2-phenyl-3,4-dihydro-2H-1,4-benzoxazine

Under an inert atmosphere, the compound obtained in Step B (3.26 g; 12.77 mmol) is dissolved in 70 ml of anhydrous tetrahydrofuran (6 ml/1 mmol), and then lithium aluminium hydride (5 eq.; 63.85 mmol; 2.42 g) is added in portions at 0° C. The mixture is stirred at ambient temperature for 16 hours, and then the solution is hydrolysed at 0° C. with 2.4 ml of water, 2.4 ml of a 15% sodium hydroxide solution and 7.2 ml of water. The solution is stirred for 30 minutes, and the salts that have formed are filtered off using a Büchner funnel and the solvent is removed under reduced pressure. The crude reaction product is purified by flash chromatography on silica gel (eluant: PE/AcOEt (8/2)). The title product is obtained in the form of a solid.
Melting point: 95–100° C.

Step D: 2-(6-Methoxy-2-phenyl-2,3-dihydro-4H-1,4-benzoxazin-4-yl)acetonitrile

The compound obtained in Step C (1.5 g; 6.22 mmol) is suspended in 25 ml of water (4 ml/1 mmol). Potassium hydrogen carbonate (10 eq.; 62.2 mmol; 5.22 g), tetrabutylammonium bromide (0.05 eq.; 0.31 mmol; 100 mg) and bromoacetonitrile (8 eq.; 49.7 mmol; 3.46 ml) are then added. The mixture is stirred vigorously at 70° C. for 16 hours. After returning to ambient temperature, the product formed is extracted with dichloromethane. The organic phase is dried over $MgSO_4$, filtered, and then concentrated under reduced pressure. The residue obtained is purified by flash chromatography on silica gel (eluant: PE/AcOEt (8/2)). The title product is obtained in the form of a solid.
Melting point: 154–156° C.

Step E: N-[2-(6-Methoxy-2-phenyl-2,3-dihydro-4H-1,4-benzoxazin-4-yl)-ethyl]acetamide The compound obtained in Step D (350 mg; 1.25 mmol) is dissolved in a Parr reactor with acetic anhydride. Raney nickel (30% by weight, 115 mg) and sodium acetate (1.5 eq.; 1.87 mmol; 154 mg) are then added. The mixture is left at 50° C. for 16 hours under a hydrogen pressure of 40 psi. After returning to ambient temperature, the solution is filtered over Celite and the filtrate is evaporated. The crude reaction product is purified by flash chromatography on silica gel (eluant: PE/AcOEt (1/9)). The title product is obtained in the form of white crystals and is recrystallised from an $Et_2O$/i-PrOH (6/4) mixture.
Melting point: 153–154° C.

| Elemental microanalysis: | | | |
|---|---|---|---|
| | C % | H % | N % |
| Calculated: | 69.92 | 6.79 | 8.58 |
| Found: | 69.94 | 6.75 | 8.59 |

EXAMPLE 24

N-[2-(6-Methoxy-2-phenyl-2,3-dihydro-4H-1,4-benzoxazin-4-yl)ethyl]benzamide

Under an inert atmosphere, the compound obtained in Step D of Example 23 is dissolved in anhydrous ether (2 ml/0.1 mmol) and then lithium aluminium hydride (1.5 eq.) is added in portions. The mixture is stirred at ambient temperature for 2 hours, and then the solution is hydrolysed, at 0° C., with water and a 15% sodium hydroxide solution. The solution is stirred for 30 minutes, and then the salts that have formed are filtered off using a Büchner funnel. The solvents are removed under reduced pressure, and the yellow oil obtained is placed under a dynamic vacuum under $P_2O_5$ for 2 hours. Without further purification, the amine obtained is used directly in the acylation reaction. Under an inert atmosphere, the amine is dissolved in distilled dichloromethane and then the solution is cooled to 0° C. Triethylamine (3 eq.), and then benzoyl chloride (1.5 eq.), are slowly added. The mixture is left at ambient temperature until the amine has disappeared, and then the organic phase is washed with water and dried over $MgSO_4$ and the solvents are removed under reduced pressure. The residue obtained is purified by flash chromatography on silica gel to yield a solid which is recrystallised from $Et_2O$/AcOEt (99/1).
Melting point: 174–175° C.

| Elemental microanalysis: | | | |
|---|---|---|---|
| | C % | H % | N % |
| Calculated: | 74.21 | 6.23 | 7.21 |
| Found: | 73.56 | 6.26 | 7.01 |

EXAMPLE 25

N-[2-(6-Methoxy-2-phenyl-2,3-dihydro-4H-1,4-benzoxazin-4-yl)ethyl]butanamide

The procedure is as in Example 24, with the replacement of benzoyl chloride with butyryl chloride. Recrystallisation from $Et_2O$/iPrOH.
Melting point: 124–125° C.

| Elemental microanalysis: | | | |
|---|---|---|---|
| | C % | H % | N % |
| Calculated: | 71.16 | 7.39 | 7.90 |
| Found: | 70.59 | 7.39 | 7.70 |

EXAMPLE 26

N-[2-(6-Methoxy-2-phenyl-2,3-dihydro-4H-1,4-benzoxazin-4-yl)ethyl]-2-furamide

The procedure is as in Example 2,4, with the replacement of benzoyl chloride with 2-furoyl chloride. Recrystallisation from Et$_2$O/AcOEt (99/1).
Melting point: 129–130° C.

| Elemental microanalysis: | | | |
|---|---|---|---|
| | C % | H % | N % |
| Calculated: | 69.83 | 5.86 | 7.40 |
| Found: | 69.22 | 5.99 | 7.12 |

EXAMPLE 27

N-[2-(6-Methoxy-2-phenyl-2,3-dihydro-4H-1,4-benzoxazin-4-yl)ethyl]cyclopropanecarboxamide The procedure is as in Example 24, with the replacement of benzoyl chloride with cyclopropanecarbonyl chloride.

EXAMPLE 28

N-[2-(6-Methoxy-2-phenyl-2,3-dihydro-4H-1,4-benzoxazin-4-yl)ethyl]-N'-phenylurea 0.011 mol of phenyl isocyanate are added to a suspension of 0.01 mol of the amine hydrochloride obtained in Example 24 (before acylation) in 5 cm$^3$ of pyridine. After stirring for 1 hour at 80° C., the reaction mixture is poured into iced water and then acidified with 1N HCl. The precipitate formed is suction-filtered off, washed, dried, and then recystallised to yield the title product.

EXAMPLE 29

N-[2-(2-Acetyl-6-methoxy-2,3-dihydro-4H-1,4-benzoxazin-4-yl)ethyl]pentanamide

Step A: 2-(2-Acetyl-6-methoxy-2,3-dihydro-4H-1,4-benzoxazin-4-yl)acetonitrile

The procedure is as in Example 23, with the replacement of 2-bromophenylacetyl chloride with 2-bromo-3-oxobutanoyl chloride in Step A.

Step B: N-[2-(2-Acetyl-6-methoxy-2,3-dihydro-4H-1,4-benzoxazin-4-yl)ethyl]pentanamide The procedure is as in Example 24, with the replacement of benzoyl chloride with pentanoyl chloride.

EXAMPLE 30

N-(2-Furylmethyl)-4-(6-methoxy-2-phenyl-2,3-dihydro-4H-1,4-benzoxazin-4-yl)butanamide Step A: 2-(6-Methoxy-2-phenyl-2,3-dihydro-4H-1,4-benzoxazin-4-yl)butanenitrile The procedure is as in Steps A, B, C and D of Example 23, with the replacement of bromoacetonitrile with 4-bromobutanenitrile in Step D.

Step B: N-(2-Furylmethyl)-4-(6-methoxy-2-phenyl-2,3-dihydro-4H-1,4-benzoxazin-4-yl)butanamide The procedure is as in Steps B and C of Example 12, with the replacement of N-methylamine with N-(2-furylmethyl)amine in Step C.

EXAMPLE 31

N-[2-(6-Cyclopropyl-2,3-dihydro-4H-1,4-benzoxazin-4-yl)ethyl]-cyclohexanecarboxamide Step A: 2-(6-Cyclopropyl-2,3-dihydro-4H-1,4-benzoxazin-4-yl)acetonitrile The procedure is as in Example 1 (Steps A–E), starting from 4-cyclopropyl-2-nitrophenol.

Step B: N-[2-(6-Cyclopropyl-2,3-dihydro-4H-1,4-benzoxazin-4-yl)ethyl]cyclohexanecarboxamide The procedure is as in Example 2, starting from the compound obtained in Step A and with the replacement of butyryl chloride with cyclohexylcarbonyl chloride.

EXAMPLE 32

N-[2-(6-Methoxy-4H-1,4-benzoxazin-4-yl)ethyl]acetamide

The procedure is as in Example 1, the compound obtained in Step D being subjected, after protection of the NH function by a Boc group ((tert-butyl)oxycarbonyl), to the action of NBS in the presence of AIBN, then NaI in acetone, to yield, after deprotection using formic acid, 6-methoxy-4H-1,4-benzoxazine.

The procedure is then as in Steps E and F of Example 1.

EXAMPLE 33

N-(2-{6-[(Methylamino)sulfonyl]-4H-1,4-benzoxazin-4-yl}ethyl)acetamide

The procedure is as in Example 32, using as starting material 4-hydroxy-N-methyl-3-nitrobenzenesulfonamide.

EXAMPLE 34

N-[2-(6-Methoxy-4H-1,4-benzoxazin-4-yl)ethyl]cyclopropanecarboxamide

The procedure is as in Example 32, using in Step F the procedure used in Example 2 with the replacement of butyryl chloride with cyclopropanecarbonyl chloride.

EXAMPLE 35

Methyl 4-{2-[(cyclopropylcarbonyl)amino]ethyl}-4H-1,4-benzoxazin-6-ylcarbamate

The procedure is as in Example 34, using as starting material methyl 4-hydroxy-3-nitrophenylcarbamate.

EXAMPLE 36

N-{2-[2-(3-Aminophenyl)-6-methoxy-4H-1,4-benzoxazin-4-yl]ethyl}-acetamide

The procedure is as in Example 23, with the replacement of bromo(phenyl)acetyl chloride with (3-aminophenyl)(bromo)acetyl chloride in Step A, and with subjection of the compound obtained in Step C to the successive action of NBS/AIBN and NaI before carrying out Steps D and E.

PHARMACOLOGICAL STUDY

EXAMPLE A

Acute Toxicity Study

Acute toxicity was evaluated after oral administration to groups each comprising 8 mice (26±2 grams). The animals were observed at regular intervals during the course of the first day, and daily for the two weeks following treatment. The $LD_{50}$, the dose that causes the death of 50% of the animals, was evaluated, and demonstrated the low toxicity of the compounds of the invention.

EXAMPLE B

Melatonin Receptor Binding Study on pars tuberalis Cells of Sheep

Melatonin receptor binding studies of the compounds of the invention were carried out according to conventional techniques on pars tuberalis cells of sheep. The pars tuberalis of the adenohypophysis is in fact characterised in mammals by a high density of melatonin receptors (Journal of Neuroendocrinology, 1, pp. 1–4, 1989).

Protocol

1) Sheep pars tuberalis membranes are prepared and used as target tissue in saturation experiments to determine the binding capacities and affinities for 2-[$^{125}$I]-iodomelatonin.

2) Sheep pars tuberalis membranes are used as target tissue in competitive binding experiments using the various test compounds in comparison with melatonin.

Each experiment is carried out in triplicate and a range of different concentrations is tested for each compound. The results, after statistical processing, enable the binding affinities of the compound tested to be determined.

Results

The compounds of the invention appear to have a strong affinity for melatonin receptors.

EXAMPLE C

1. Melatonin $mt_1$ and $MT_2$ receptor binding study

The $mt_1$ or $MT_2$ receptor binding experiments are carried out using 2-[$^{125}$I]-iodomelatonin as reference radioligand. The radioactivity retained is determined using a liquid scintillation counter.

Competitive binding experiments are then carried out in triplicate using the various test compounds. A range of different concentrations is tested for each compound. The results enable the binding affinities ($IC_{50}$) of the compounds tested to be determined.

2. Study of binding to melatonin $MT_3$ binding sites

The experiments on binding to $MT_3$ sites are carried out on hamster brain membanes using 2-[$^{125}$I]-iodomelatonin as radioligand. The membranes are incubated for 30 minutes with 2-[$^{125}$I]-iodomelatonin at a temperature of 4° C. and at various concentrations of the test compounds. After incubation, the membranes are rapidly filtered and then washed with cold buffer with the aid of a filtration system. The bound radioactivity is measured using a scintillation counter. The $IC_{50}$ values (concentration that inhibits specific binding by 50%) are calculated from competition curves according to a non-linear regression model.

Thus, the $IC_{50}$ values found for the compounds of the invention show binding for one or other of the melatoninergic binding sites, those values being $\leq 10$ $\mu$M.

EXAMPLE D

Action of the Compounds of the Invention on the Circadian Rhythms of Locomotive Activity of the Rat The involvement of melatonin in influencing the majority of physiological, biochemical and behavioural circadian rhythms by day/night alternation has made it possible to establish a pharmacological model for research into melatoninergic ligands.

The effects of the compounds are tested in relation to numerous parameters and, in particular, in relation to the circadian rhythms of locomotive activity, which are a reliable indicator of the activity of the endogenous circadian clock.

In this study, the effects of such compounds on a particular experimental model, namely the rat placed in temporal isolation (permanent darkness), are evaluated.

Experimental Protocol

One-month-old male rats are subjected, as soon as they arrive at the laboratory, to a light cycle of 12 hours of light per 24 hours (LD 12:12).

After 2 to 3 weeks' adaptation, they are placed in cages fitted with a wheel connected to a recording system in order to detect the phases of locomotive activity and thus monitor the nychthemeral (LD) or circadian (DD) rhythms.

As soon as the rhythms recorded show a stable pattern in the light cycle LD 12:12, the rats are placed in permanent darkness (DD).

Two to three weeks later, when the free course (rhythm reflecting that of the endogenous clock) is clearly established, the rats are given a daily administration of the compound to be tested.

The observations are made by means of visualisation of the rhythms of activity:

influence of the light rhythm on the rhythms of activity, disappearance of the influence on the rhythms in permanent darkness, influence by the daily administration of the compound; transitory or durable effect.

A software package makes it possible:

to measure the duration and intensity of the activity, the period of the rhythm of the animals during free course and during treatment, possibly to demonstrate by spectral analysis the existence of circadian and non-circadian (for example ultradian) components.

Results

The compounds of the invention clearly appear to have a powerful action on the circadian rhythm via the melatoninergic system.

EXAMPLE E

Light/Dark Cage Test

The compounds of the invention are tested on a behavioural model, the light/dark cage test, which enables the anxiolytic activity of the compounds to be revealed.

The equipment comprises two polyvinyl boxes covered with Plexiglas. One of the boxes is in darkness. A lamp is placed above the other box, producing a light intensity of approximately 4000 lux at the centre of the box. An opaque plastics tunnel separates the illuminated box from the dark box. The animals are tested individually for a session of 5 minutes. The floor of each box is cleaned after each session. At the start of each test, the mouse is placed in the tunnel, facing the dark box. The time spent by the mouse in the illuminated box and the number of passages through the tunnel are recorded after the first entry into the dark box.

Following administration of the compounds 30 minutes before the start of the test, the compounds of the invention significantly increase the time spent in the illuminated cage and the number of passages through the tunnel, which demonstrates the anxiolytic activity of the compounds of the invention.

EXAMPLE F

Activity of the Compounds of the Invention on the Caudal Artery of the Rat

The compounds of the invention were tested in vitro on the caudal artery of the rat. Melatoninergic receptors are present in those vessels, thus providing a relevant pharmacological model for studying melatoninergic ligand activity. Stimulation of the receptors can induce either vasoconstriction or dilation depending upon the arterial segment studied.

Protocol

One-month-old rats are accustomed to a light/dark cycle of 12 h/12 h over a period of 2 to 3 weeks.

After sacrifice, the caudal artery is isolated and maintained in a highly oxygenated medium. The arteries are then cannulated at both ends, suspended vertically in an organ chamber in a suitable medium and perfused via their proximal end. The pressure changes in the perfusion flow enable evaluation of the vasoconstrictive or vasodilatory effect of the compounds.

The activity of the compounds is evaluated on segments that have been pre-contracted by phenylephrine (1 μM). A concentration/response curve is determined non-cumulatively by the addition of a concentration of the test compound to the pre-contracted segment. When the effect observed reaches equilibrium, the medium is changed and the preparation is left for 20 minutes before the addition of the same concentration of phenylephrine and a further concentration of the test compound.

Results

The compounds of the invention significantly modify the diameter of the caudal arteries pre-constricted by phenylephrine.

EXAMPLE G

Pharmaceutical Composition: Tablets

| | |
|---|---|
| 1000 tablets each comprising a dose of 5 mg of N-[2-(6-methoxy-2,3-dihydro-4H-1,4-benzoxazin-4-yl)ethyl]benzamide (Example 6) | 5 g |
| wheat starch | 20 g |
| maize starch | 20 g |
| lactose | 30 g |
| magnesium stearate | 2 g |
| silica | 1 g |
| hydroxypropyl cellulose | 2 g |

We claim:

1. A compound selected from those of formula (I):

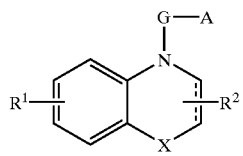

(I)

wherein:

$R^1$ represents halogen or R, OR, SR, SO$_2$NRR', —NRR',

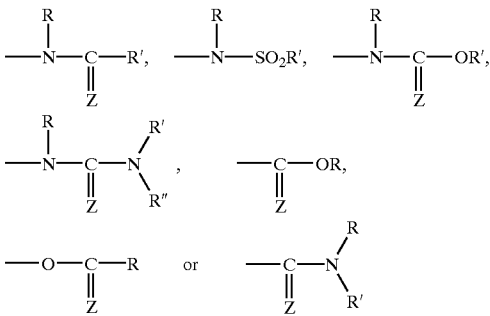

wherein Z represent sulphur or oxygen and R, R' and R", which are identical or different, represent hydrogen or unsubstituted or substituted, linear or branched ($C_1$–$C_6$)alkyl, unsubstituted or substituted, linear or branched ($C_2$–$C_6$)alkenyl, unsubstituted or substituted, linear or branched ($C_2$–$C_6$)alkynyl, unsubstituted or substituted ($C_3$–$C_8$)cycloalkyl, unsubstituted or substituted ($C_3$–$C_8$)cycloalkyl-($C_1$–$C_6$)alkyl in which alkyl is linear or branched, aryl, aryl($C_1$–$C_6$)alkyl in which alkyl is linear or branched, heteroaryl or heteroaryl-($C_1$–$C_6$)alkyl in which alkyl is linear or branched, and wherein (R and R') or (R' and R") may together form, with the nitrogen atom carrying them, morpholinyl, piperidinyl, piperazinyl or pyrrolidinyl, G represents an alkylene chain containing from 2 to 4 carbon atoms when A represents

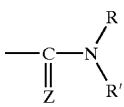

and from 1 to 4 carbon atoms in all other cases,

G being optionally substituted by R, OR, COR or COOR (wherein R is as defined hereinbefore), A represents

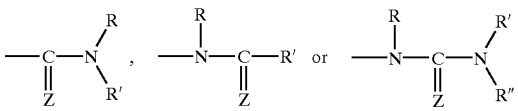

(wherein R, R', R" and Z are as defined hereinbefore), $R^2$ represents halogen or R, OR, COR, COOR or OCOR (wherein R is as defined hereinbefore), X represents oxygen, the symbol ≡≡≡ denotes that the bond is single or double, the valency of the atoms being respected, wherein:

the term "substituted" applied to "alkyl", "alkenyl", "alkynyl" or "cycloalkyl" denotes that those groups may be substituted by one or more identical or different groups selected from hydroxy, alkoxy, alkyl, polyhaloalkyl, amino (unsubstituted or substituted by one or two linear or branched ($C_1$–$C_6$)alkyl groups) and halogen, the term "substituted" applied to "cycloalkylalkyl" denotes that the cyclic moiety of the group is substituted by one or more identical or different groups selected from hydroxy, alkoxy, alkyl, polyhaloalkyl, amino (unsubstituted or substituted by one or two linear or branched ($C_1$–$C_6$)alkyl groups) and halogen, "aryl" denotes phenyl, naphthyl or biphenyl, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, —$CONH_2$ (wherein one or two hydrogen atoms can be replaced with a ($C_1$–$C_6$)alkyl group) and halogen, "heteroaryl" denotes any mono- or bi-cyclic aromatic group containing from one to three hetero atoms selected from oxygen, sulphur and nitrogen, those groups being unsubstituted or substituted by one or more identical or different groups selected from hydroxy, alkoxy, alkyl, amino, alkylamino, dialkylamino, nitro, cyano, polyhaloalkyl, formyl, carboxy, alkoxycarbonyl, —$CONH_2$ (wherein one or two hydrogen atoms can be replaced with a ($C_1$–$C_6$) alkyl group) and halogen, their enantiomers and diastereoisomers, and addition salts thereof with a pharmaceutically acceptable acid or base.

2. A compound of claim 1, wherein X represents oxygen.

3. A compound of claim 1 which is (dihydro)benzoxazine compounds.

4. A compound of claim 1, wherein $R^1$ represents OR.

5. A compound of claim 1, wherein $R^2$ represents hydrogen.

6. A compound of claim 1, wherein $R^2$ represents unsubstituted or substituted phenyl.

7. A compound of claim 1, wherein G represents $(CH_2)_n$ in which n is 2 or 3.

8. A compound of claim 1, wherein A represents NHCOR.

9. A compound of claim 1, wherein A represents CONHR.

10. A compounds of claim 1 selected from N-[2-6-hydroxy-2,3-dihydro-4H-1,4-benzoxazin-4-yl)ethyl] acetamide, N-[2-(6-methoxy-2,3-dihydro-4H-1,4-benzoxazin-4-yl)ethyl]acetamide, N-[2-(6-methoxy-2,3-dihydro-4H-1,4-benzoxazin4-yl)ethyl]-butanamide, N-[2-(6-methoxy-2,3-dihydro-4H-1,4-benzoxazin-4-yl)ethyl]-3-butenamide, N-[2-(6-methoxy-2,3-dihydro-4H-1,4-benzoxazin-4-yl)ethyl]cyclopropanecarboxamide, N-[2-(6-methoxy-2,3-dihydro-4H-1,4-benzoxazin-4-yl)ethyl]-2-furamide, N-[2-(6-methoxy-2,3-dihydro-4H-1,4-benzoxazin-4-yl)ethyl]benzamide, N-[2-(6-hydroxy-2,3-dihydro-4H-1,4-benzoxazin-4-yl)ethyl]-2-furamide, its enantiomers and diastereoisomers, and also addition salts thereof with a pharmaceutically acceptable acid or base.

11. A compounds of claim 1 selected from N-[2-(6-methoxy-3-phenyl-2,3-dihydro-4H-1,4-benzoxazin-4-yl) ethyl]acetamide, N-[2-(6-methoxy-3-phenyl-2,3-dihydro-4H-1,4-benzoxazin-4-yl)ethyl]benzamide, N-[2-(6-methoxy-3-phenyl-2,3-dihydro-4H-1,4-benzoxazin-4-yl) ethyl]-2-furamide, N-[2-(6-methoxy-3-phenyl-2,3-dihydro-4H-1,4-benzoxazin-4-yl)ethyl]butanamide, N-[2-(6-methoxy-2-phenyl-2,3-dihydro-4H-1,4-benzoxazin-4-yl) ethyl]acetamide, N-[2-(6-methoxy-2-phenyl-2,3-dihydro-4H-1,4-benzoxazin-4-yl)ethyl]-2-furamide, N-[2-(6-methoxy-2-phenyl-2,3-dihydro-4H-1,4-benzoxazin-4-yl) ethyl]benzamide, N-[2-(6-methoxy-2-phenyl-2,3-dihydro-4H-1,4-benzoxazin-4-yl)ethyl]butanamide, N-[2-(6-methoxy-2-phenyl-2,3-dihydro-4H-1,4-benzoxazin-4-yl) ethyl]cyclopropanecarboxamide, its enantiomers and diastereoisomers, and also addition salts thereof with a pharmaceutically acceptable acid or base.

12. A method for treating a living animal body afflicted with a condition selected from cardiovascular pathologies, sleep disorders, melancholia, and seasonal affective disorders comprising the step of administering to the living animal body an amount of a compound of claim 1 which is effective for alleviation of the condition.

13. A pharmaceutical composition useful for treating a condition selected from cardiovascular pathologies, sleep disorders, melancholia, and seasonal affective disorders, comprising, as active principle an effective amount of a compound of claim 1 together with one or more pharmaceutically acceptable excipients or vehicles.

* * * * *